(12) United States Patent
Birthisel et al.

(10) Patent No.: US 7,850,758 B2
(45) Date of Patent: Dec. 14, 2010

(54) SAFENED INSECTICIDE MATTER

(75) Inventors: Timothy D. Birthisel, Perrysburg, OH (US); James R. Lynch, Toledo, OH (US); Robin Smith, Austin, TX (US)

(73) Assignee: The Andersons, Inc., Maumee, OH (US)

( * ) Notice: Subject to any disclaimer, the term of this patent is extended or adjusted under 35 U.S.C. 154(b) by 606 days.

(21) Appl. No.: 11/623,993

(22) Filed: Jan. 17, 2007

(65) Prior Publication Data

US 2007/0163317 A1      Jul. 19, 2007

Related U.S. Application Data

(60) Provisional application No. 60/759,362, filed on Jan. 17, 2006.

(51) Int. Cl.
    *A01N 25/26* (2006.01)
(52) U.S. Cl. .................................. 71/64.1; 71/64.02
(58) Field of Classification Search .................. 71/64.1, 71/64.02
    See application file for complete search history.

(56) References Cited

U.S. PATENT DOCUMENTS

| | | | |
|---|---|---|---|
| 3,223,518 A | 12/1965 | Hansen | |
| 4,019,890 A | 4/1977 | Fujita et al. | |
| 4,033,745 A * | 7/1977 | Moore | 71/28 |
| 4,343,790 A | 8/1982 | Pasarela | |
| 5,004,614 A * | 4/1991 | Staniforth | 424/466 |
| 5,127,933 A * | 7/1992 | Hallett | 71/5 |
| 5,169,644 A | 12/1992 | Mölls et al. | |
| 5,186,732 A | 2/1993 | Thompson et al. | |
| 5,326,573 A | 7/1994 | Antfang et al. | |
| 5,346,704 A | 9/1994 | Lajoie | |
| 5,472,474 A * | 12/1995 | Nakazono | 71/12 |
| 5,589,577 A * | 12/1996 | Peltonen et al. | 536/22.1 |
| 5,652,196 A | 7/1997 | Luthra et al. | |
| 5,698,212 A | 12/1997 | Hagiwara | |
| 5,849,060 A * | 12/1998 | Diping et al. | 71/64.07 |
| 6,221,375 B1 | 4/2001 | Howse | |
| 6,407,225 B1 * | 6/2002 | Mang et al. | 536/123.1 |
| 6,656,882 B2 * | 12/2003 | Tijsma et al. | 504/101 |
| 6,682,751 B1 | 1/2004 | Hargrove et al. | |
| 6,777,524 B1 * | 8/2004 | Shimizu et al. | 528/76 |
| 6,977,033 B2 * | 12/2005 | Becker et al. | 204/450 |
| 6,987,082 B2 | 1/2006 | Tijsma et al. | |
| 7,052,708 B2 * | 5/2006 | O'Leary | 424/405 |
| 7,070,795 B1 * | 7/2006 | Botts et al. | 424/409 |

* cited by examiner

*Primary Examiner*—Timothy C Vanoy
*Assistant Examiner*—Michelle Hou
(74) *Attorney, Agent, or Firm*—Gifford, Krass, Sprinkle, Anderson & Citkowski, P.C.

(57) ABSTRACT

A particle is provided with simultaneous delivery of a fertilizer and an active agent that when adhered to foliage causes a chemical burn thereto. A hydrophobic coating is provided intermediate between the fertilizer core and the active agent to inhibit moisture absorption by the particle that renders the particle tacky and therefore adherent to target foliage. The active agent granule is adhered to the hydrophobic coating or at least partially embedded therein based on the nature of the formation process. The particle is also provided that includes a second fertilizer layer exterior to the hydrophobic coating with the second fertilizer layer is substantially devoid of water soluble nitrogen compounds. Active agent granules are then adhered to the second fertilizer layer. The resultant particles reduce chemical burning associated with combined fertilizer and active agent usage, especially under dispersant conditions of high temperature and high

US 7,850,758 B2

SAFENED INSECTICIDE MATTER

CROSS-REFERENCE TO RELATED APPLICATIONS

Figure 1A:
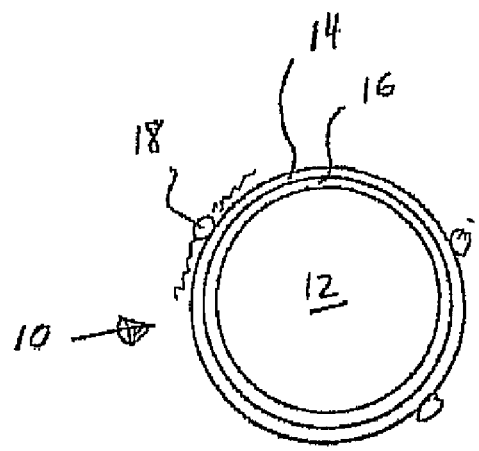

This application is a non-provisional application that claims priority benefit of U.S. provisional application Ser. No. 60/759,362, filed 17 Jan. 2006; the contents of which are hereby incorporated by reference.

FIELD OF THE INVENTION

The present invention in general relates to soluble and/or dispersible particles which simultaneously promote growth of a crop plant while inhibiting a plant pest or weed growth, and in particular, relates to particle coatings that reduce chemical burning of the target plant as a result of preventing contact between the phytotoxic agent and the target crop plant foliage.

BACKGROUND OF THE INVENTION

A problem associated with conventional soluble fertilizers such as urea is that the fertilizer particles become tacky when applied under high humidity conditions. Critical relative humidity values for a variety of fertilizer products has been compiled and shows that the application of fertilizer products at a critical relative humidity at 30° C. of above 40% causes the particles to become tacky [Manual for Determining the Physical Properties of Fertilizer, $2^{nd}$ Edition, International Fertilizer Development Center, Muscle Shoals, Ala., February, 1993, pp. 5-7. Tackified fertilizer particles associated with a degree of hydration is known to cause phytotoxicity and the rapid depletion of nutrients from the particle through leaching. An additional handling problem associated with hygroscopic fertilizer particles is that the particular tends to mass into a cake that impedes in a form particle distribution onto soil.

Attempts to encapsulate a fertilizer particle in a coating to improve humidity stability have included sulfur coating as exemplified in U.S. Pat. No. 3,342,577; VOC solvated polymer resin spray, as exemplified in U.S. Pat. No. 3,475,154; epoxy resin cure on the particles surfaces, as exemplified in U.S. Pat. Nos. 3,264,088 and 3,259,482; and multiple layer coatings, as exemplified in U.S. Pat. No. 5,698,002.

While attempts to reduce the moisture sensitivity of fertilizer particles containing hygroscopic plant nutrients has proven somewhat successful, the use of such a coating is complicated when fertilizer particle surface is decorated with an active agent intended to inhibit target plant pests or weed growth. The inclusion of a surface active agent on hygroscopic fertilizer particle, the particle absorption of even a small amount of water that would otherwise not lead to fertilizer release associated with chemical burning, induces phytotoxicity associated with a chemical burn caused by active agent adhesion onto target plant foliage. In applying the active agent surface decorated fertilizer particle, a conventional formulation to turf under even moderate humidity conditions, results in undesired turf effects, such as a tire tracking, discoloration, and thinning, with these problems being compounded when the material is applied to closely mowed hybrid Bermudagrass, Bentgrass, Bluegrass, Fescue, St, Augustine, Ryegrass, or other grass, depending on the phytotoxic characteristic of the active agent.

Since studies have shown that the same concentration of herbicide granules applied directly to soil on non-tackified fertilizer particles do not induce chemical burns on the target foliage, there exists a need to preclude active agent granule, powder, or liquided active agent decorating hygroscopic fertilizer particle from becoming adhered to target foliage. There further exists a need for the development of an intermediate coating between the hygroscopic fertilizer particle and surface decorating active agent granule, powder, or liquid that performs dual functions of rendering hygroscopic fertilizer particle slower towards water absorption while simultaneously adhering active agent granules. While prior art hygroscopic fertilizer particle coatings have succeeded in providing the first attribute of this need, the second attribute has remained lacking.

SUMMARY OF THE INVENTION

A particle is provided for the simultaneous delivery of a fertilizer and an active agent that when adhered to foliage causes a chemical burn thereto. A hydrophobic coating is provided intermediate between the fertilizer core and the active agent to inhibit moisture absorption by the particle that renders the particle tacky and therefore adherent to target foliage. The active agent granule is adhered to the hydrophobic coating or at least partially embedded therein based on the nature of the formation process.

The particle is also provided with a second fertilizer layer exterior to the hydrophobic coating with the proviso of at the second fertilizer layer is substantially devoid of water soluble nitrogen compounds. Active agent granules are then adhered to the second fertilizer layer. The resultant particles reduce chemical burning associated with combined fertilizer and active agent usage, especially under dispersant conditions of high temperature and high humidity.

BRIEF DESCRIPTION OF THE DRAWINGS

FIG. 1A is a cross-sectional view of an inventive particle with active agent granules contacting a hydrophobic coating, with the relative dimensions of the fertilizer core, optional friable layer, coating, and active agent granules being distorted for visual clarity;

FIG. 1B is a cross-sectional view of an inventive particle with active agent granules partially embedded in the hydrophobic coating, with the relative dimensions of the fertilizer core, optional friable layer, coating, and active agent granules being distorted for visual clarity;

FIG. 1C is a cross-sectional view of an inventive particle with active agent granules fully embedded in the hydrophobic coating, with the relative dimensions of the fertilizer core, optional friable layer, coating, and active agent granules being distorted for visual clarity; and FIG. 2 is a cross-sectional view of an alternate inventive particle in which surface decorating granules are at least in part embedded within the coating with the relative dimensions of the fertilizer core, optional friable layer, coating, and active agent granules being distorted for visual clarity.

DETAILED DESCRIPTION OF THE PREFERRED EMBODIMENTS

The present invention has utility as a plant growth promoting particle that simultaneously delivers fertilizer and an active agent with an intermediate coating between a fertilizer core and active agent surface granule that precludes chemical burning associated with active agent granule adhesion to target plant foliage.

Referring now to FIG. 1, an inventive particle is depicted generally at 10. Particle 10 includes a conventional fertilizer core 12. The fertilizer core 12 has a diameter typically between 5 and 40 mesh (SGN's of 300-50) and preferably between 6 and 40 mesh (SGN's of 250-50). More preferably, the fertilizer core 12 has a diameter of between 2:1 and 1:1, or may otherwise be described as granular, vs. oblong or platy in shape Most preferably, the fertilizer core 12 has an aspect ration between a long axis (diameter) and a shortest orthogonal axis of between 1.5:1 and 1:1, or may otherwise be described as roughly spherical. Exemplary fertilizer core N—P—K contributing constituents illustratively includes urea, ammonium nitrate, ammonium sulfate, ammonium phosphates, varying degrees of ammonation, potassium chloride, potassium nitrate, potassium sulfate, ammonium polyphosphates, potash, phosphate rock, nitrophosphate, and combinations thereof. It is also appreciated that a fertilizer core 12 readily incorporates other substances stimulative of target plant growth and illustratively include soil conditioners, trace elements, plant hormones active in the target plant, and dust control, flowability and/or storability additives. Additionally, fertilizer core 12 optionally includes conventional fillers, binders, and additives as exemplified in U.S. Pat. No. 6,884,756. Preferably, the fertilizer core 12 includes at least 20 units of N—P—K nutrients, where a "unit" is used herein to define an increment of 1% of a guaranteed plant nutrient as defined by the American Association of Plant Food Control Officials (AAPFCO), which is the uniform standards-setting association of state fertilizer control officials in the United States.

Underlying the fertilizer core 12 is a coating 14. The coating 14 is hydrophobic and illustratively includes polyurethane, polyvinyl acetate, ethoxylated cellulose, polyvinyl pyrrolidone, polyalkyl acrylates, polyalkylenes, latexes, and pine rosins. The coating 14 is applied to a thickness such that the fertilizer core 12 remains stable for at least 0.5 seconds of immersion in a 20° C. water bath, and preferably for between one and five minutes. As used herein, fertilizer core stability is defined as greater than 70% by weight of the water-soluble fertilizer core constituents remaining spatially retained within the coating 14.

As used herein, water-soluble fertilizer core constituent "is defined to include N—P—K containing a composition having a solubility in water at 20° C. of greater than 0.1 grams per milliliter.

A test for fertilizer core soluble constituent solubility includes fully formulating an inventive particle and placing a pre-weighed quantity of such particles into a water bath of 20° C. having a weight of 100 times that of the inventive particles with the inventive particles being contained within a pre-weighed wire cage. With the particles immersed in the water bath for a pre-selected amount of time, such as five minutes, the basket is removed and the contents dried to a constant weight with a vacuum oven set at a constant temperature between 25-30° C. The weight differential before and after water immersion determines the remaining quantity of soluble nutrients after composition for the tere of the wire basket and surface decorating granule removal. The water bath is also analyzed for soluble N—P—K concentration based on AOAC Official Methods of Analysis (1984), various test protocols found in Chapter 2, based on whether the fertilizer core contained nitrogen, phosphorous, potassium, or combinations thereof, and based upon the specific fertilizer composition. It is appreciated that the thickness of the coating 14 necessary to provide the degree of water bath stability required of the present invention is in part dependant on the nature of the polymeric coating. Preferably, the coating 14 is applied as a single layer, as opposed to a compositionally graded or multiple application coatings to build-up the thickness of coating 14. Typical thicknesses of coating 14 range from 0.5 to 1000 microns and preferably between 1 and 500 microns. The coating 14 typically represents between 0.5 and 50 total weight percent of an inventive particle. Optionally, a friable layer 16 is applied onto the fertilizer core and overlayered or underlain with coating 14. A friable layer 16 operative herein illustratively includes elemental sulfur, waxes, oils that are solids at 20° C., rubber, clay, and hardened candy. The thickness of friable layer 16 is typically between 1 and 500 microns and preferably between 10 and 100 microns. The friable layer 16 typically constitutes between 1 and 25 total weight percent of the inventive particle.

An active agent granule, powder, or liquid 18 is present on the exterior of an inventive particle 10. The active agent is added virtually without limit and includes any active agent granule, active agent granule, powder, or liquid, herbicide, insecticide, fungicide, growth regulator, nematicide, or other biologically active agent or pesticide, and has the property of being phytotoxic locally or systemically when placed on the foliage of a target plant. Representative herbicide active agents illustratively include dintroanilines such as benefin, trifluralin, pendimethalin, and prodiamine, oxadiazoles such as oxadiazon, triazines such as atrazine and simazine, triazolinones such as carfentrazone and sulfentrazone, Aryloxyphenoxy propionates, Arylaminopropionic acid, Cineole (such as cinmethylin), Cyclohexanediones, Sulfonylureas such as trifloxysulfuron and metsulfuron-methyl, Imidazolinones, Pyrimidinylthio-benzoate, Triazolopyrimidine, Pyridazine, Phenoxys (or Phenoxies), Benzoic acids, Carboxylic acids (such as DCPA, clopyralid, trichloroacetic acid, and flouroxypyr), Quinoline carboxylic acid, Semicarbazone, Triazinones, Uracils, Pyridazinone, Phenyl-carbamates, Nitriles, Benzothiadiazoles, Organoarsenicals, Phenyl-pyridazine, Triketones such as mesotrione, Ureas and substituted ureas (such as diuron, linuron, siduron, tebuthiuron, dymron etc.), Amide (such as propanil and bromobutide), Thiocarbamates, Pyrazolium (such as difenzoquat), Phosphoric acid compounds (such as glufosinate-ammonium and glyphosate), Triazole, Pyridazinone, Nicotinanilide, Pyridinone (such as fluridone), Isoxazolidinone, Diphenylethers, N-phenylphthalimides, Oxadiazole, Triazolinone, Chloroacetamides, Oxyacetamides, Phthalamate, Phthalamate Semicarbazone, Nitrile, N-phenylphthalimides, Oxadiazole, Triazolinone, Acetamides, Benzoylisoxazole, Isoxazole, Pyrazole, Pyrazolium, Triketone, and Benzofuran, various ALS inhibitors, and plant extract herbicides such as the allelopathic exudates of various plants.

Representative microbicidal and fungicidal active agents illustratively include plant and general disease control agents including fungicides, fungistats, antibiotics and bacteriocides of the following chemical families and functional groupings; various Acetamides, Sterol Inhibitors or Demethylase Inhibitors, Dicarboximides (such as Iprodione), Phthalides, Phthalmic acids, Triadiazoles, Isophthalates, Triazines, Triconazoles, Strobilurins, Benzimidazoles, Benzithiazoles, Dithiocarbamates, Carboxamides, Carboxides or Anilides, Chlorphenyls, Indolecarboxylic acids, Isoxazoles, Imidazoles, Oxazolinediones, Guanidines, Diguanidines, Piperidines, Pyridines, Sulfenamides, Sulfonamides, Quinolines, Cyanoimidazoles, Pyrazoles, Pyrrolecarbonitriles, Spiroketalamines, Thiazoles, various chemical families of Oomycete (Pythium) Fungicides, Nitriles, chlorinated hydrocarbons, phenylpyrroles, polyoxins, Pyridazinones, mycotoxins (e.g. penicillin) or other antibiotics (e.g. streptomycin, Kasugamycin, Blasticidin, Polyoxins, Validamycin, Mildiomycin, and oxytetracyline), Morpholines, other organic compounds such as Piperalin, piperazine derivatives and Tolylfluanid, Bronopol, organic compound mixtures (e.g. Bacticin and Harpin protein), organic acids such as cinnamic acid and its derivatives, bacteria such as *Agrobacterium radiobacter; Bacillus subtilus, Erwinia carotovora, Pseudomonas flourescens* and *P. chlorophis*, and any varieties or strains thereof, fungi such as *Candida oleophila, Fusarium, Tricoderma, Gliocladium, Streptomyces*, and *Ampelomyces* and any species, varieties or strains thereof, and viruses such as Tomovax.

For purposes of this invention, Plant growth regulators are ingredients such as trinexepac-ethyl, gibberellic acid, gibberellins, cytokinins, benzyladenine, glycines, quinolenes, phosphoric acid compounds, organic carbamates, quaternary ammonium compounds, acetamides, Ethychlozate, azoles, paclobutrazol, anilides, pyradazidine, pyrimidines, Napthaleneacetamide, phthalmides, phenoxies, pyrimidines, hybridizing agent, biostimulants, seaweed extracts, and herbicides (typically at low use rates), phthalmides, phenoxies, organic or carboxylic acids (e.g. gamma amino butyric acid and L-glutamic acid, Napthalene acetic acid, Clofencoet, Sintofen, nicotinic acids), and herbicides (typically at low use rates).

For purposes of this invention, other pesticides include animal and bird repellants, bitter flavors, irritants, and malodorous ingredients, Molluscicides (e.g., slugs and snails), Nematicides, Rodenticides, Defoliants, Chemosterilants, plant defense boosters (Harpin protein and Chitosan) Desiccants (may also be used as a harvest aid), and other beneficial or detrimental agents applied to plant or other surfaces.

For purposes of this invention, other protectants and beneficial ingredients include attractants, baits, herbicide safeners, antidessicants, antitranspirants, frost prevention aids, inoculants, dyes, brighteners, markers, synergists, pigments, UV protectants, antioxidants, leaf polish, pigmentation stimulants and inhibitors, surfactants, moisture retention aids, humic acids and humates, lignins and lignates, Molluscicides (e.g., slugs and snails), Nematicides, Rodenticides, defoliants, desiccants, sticky traps, and IPM lures.

It is appreciated that multiple active pesticide agents are readily formulated within a pesticide active agent granule, powder, or liquid operative herein. Active agent granule 18 presents an active agent granule, powder, or liquid of pure active agent, active agent compounded with inner fillers, dust control and flow aids, solvents, surfactants, and/or other adjuvants, alone or in combination with up to several other active agents. An active agent granule 18 forming a surface dusting or coating to an inventive particle 10 includes any conventional herbicide, insecticide, fungicide, nematicide, or other pesticide formulated as an active agent granule, powder, or liquid that has the property of inducing a phytotoxic chemical burn locally or systemically to target plant foliage upon such granules 18 being adhered to the foliage. Preferably, active agent granule 18 is sized such that the granule grain diameter has a mean particle diameter of less than 1% that of the combined supporting core and intermediate layers diameter. More preferably, the pesticide active agent granule, or powder has a mean diameter of less than 0.01% that of the combined supporting core and intermediate layers diameter, and the coating may be infinitesimally thin if applied as a liquid.

Exemplary soil nutrients include calcium, magnesium, sulfur, iron, manganese, copper, zinc; oxides thereof; salts thereof, and a combination thereof.

Exemplary amendment materials include humic acid, blood meal, bone meal, seed meal, feather meal, soy meal, meat meal, animal waste, activated sludge, hydrolyzed animal hair, a fish byproduct, chitin, composts and a combination thereof. In addition, a fertilizer particle optionally includes an additive to aid in particle formation illustratively including an anti-dust agent, an anti-caking agent, a filler, a preservative, and a combination thereof.

A biological factor or biostimulant is optionally included as an active ingredient in an amount ranging from 0.0005% to 10% by weight of the total weight of the particle. In a more preferred embodiment, the biological factor or biostimulant active ingredient is present in an amount ranging from 0.01% to 5% by weight of the total weight of the particle. In a still more preferred embodiment, the biological factor or biostimulant active ingredient is present in an amount ranging from 0.25% to 1% by weight of the total weight of the particle.

Biostimulants are substances that promote plant survival and health and illustratively include plant growth hormones and plant growth regulators such as cytokinins, auxins, gibberellins, ethylene, absisic acid and a combination of these.

The preferred longest linear dimension for an active agent granule 18 is between 3 and 100 microns. It is appreciated that for a spherical granule, the longest linear dimension is equivalent to the granule diameter.

An inventive particle 10 is formed through the initial creation of a core 12 through the use of conventional techniques. Techniques commonly used to form a core 12 containing fertilizer and any other optional adjuvants illustratively includes drum or pan agglomeration, pastille formation, molten droplet spray, crystallization, extrusion, and compaction. Techniques for the formation of a fertilizer pellet are provided in Granulated Fertilizers, Robert A Hendrie, Noyes Data Corporation, Park Ridge, N.J., 1976. The application of a friable layer 16 and or a coating 14 occurs through spray application of a solvated polymer, liquid monomer and any necessary catalyst to polymerize material onto a core, or with resort to core enrobement in a molten stream of material through which the core is conveyed. It is appreciated that enrobement is particularly preferred in the application of thermoplastic materials inclusive of hard candy by one or more of low pressure, hydraulic, or pneumatic spraying, and or the application of fluidized or mass-flow solid components, usually under conditions of added heating followed by shaping or polishing operations, screening, cooling and/or drying. Tumbling a particle terminating in hardened coating 14 in the presence of granule, powder, or liquid or slurry of granules, with or without a liquid spray application is sufficient to form inventive particle 10.

Figure 1B:
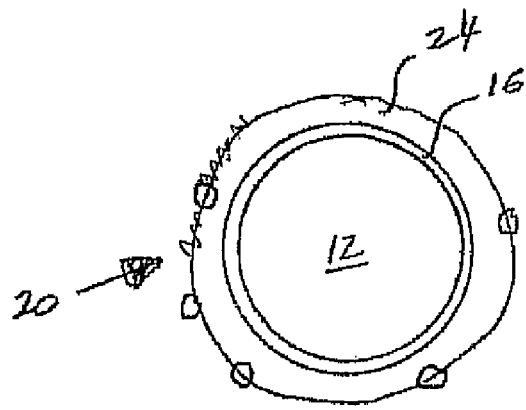

Alternatively, liquids, powder, and/or granules 18 are contacted with a core covered with coatings still in a flowable state so as to at least partially embed granules 18 in the coating 24, as shown in FIG. 1B for particle 20, where previous reference numerals used correspond to the descriptions provided to those referenced with respect to FIG. 1A.

Figure 1C:
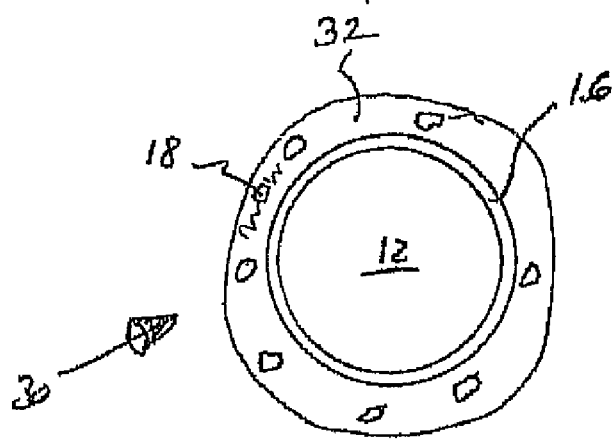

Referring now to FIG. 1C will likely most correspond to descriptions of those reference numerals with respect to FIG. 1A, an inventive particle 30 has a hydrophobic coating 32 formed of the same materials as coating 14 with respect to FIG. 1A. Coating 32 is applied with granules 18 dispersed therein resulting in active agent granules 18 wholly embedded within the coating 32. It is appreciated that the coating 32 is applied thoroughly to a thickness greater than twice the average diameter of granule 18 and preferably between 2 and 4 times the average diameter of granule 18.

Figure 2:
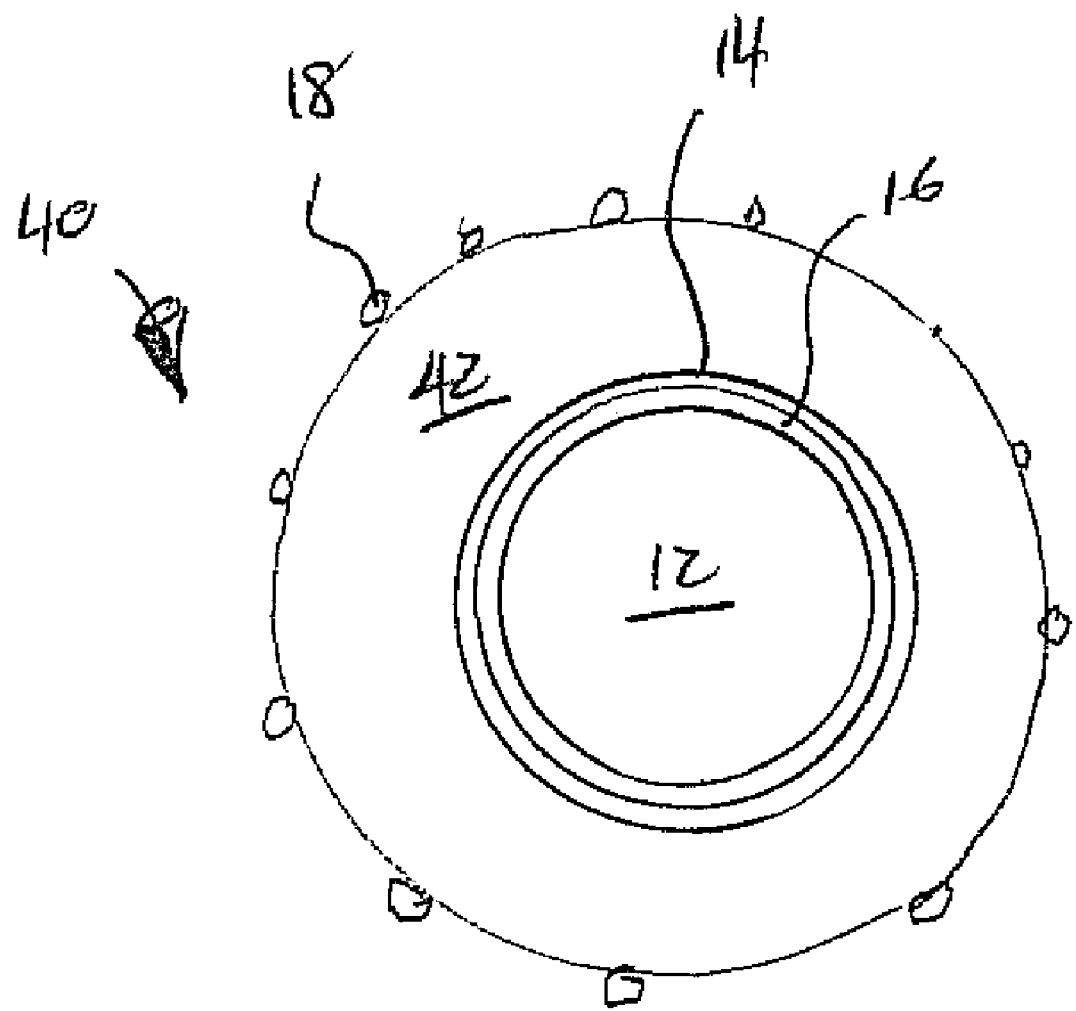

Referring now to FIG. 2, an inventive particle 40 is shown with like numerals corresponding to those described previously with respect to FIG. 1A. The particle 40 is a fertilizer core 12 surrounded by a coating 14 with the optional friable layer 16 intermediate between the core 12 and the coating 14. External to the coating 14 is an outer layer of fertilizer 42.

Activating powder, liquid, and/or granules 18 decorate the surface of the second fertilizer layer 42. The second fertilizer layer 42 is independent of a water soluble nitrogen-containing fertilizer component that only contains the comparatively less hygroscopic potassium and phosphate sources held here in exemplary potassium and/or phosphorous-containing components of fertilizer core 12. Preferably, the secondary fertilizer layer 42 is composed of potash. The secondary fertilizer layer 42 typically contains between 1 and 10 units of active potassium or phosphorous.

The present invention is further illustrated with respect to the following non-limiting examples. These examples are not intended to limit the scope of the appended claims.

Example 1

As a control, particle size as 215 SGN sized particle fertilizer 22-0-10 with coated nitrogen provided through urea and/or sulfur coated urea, potassium being provided through potassium chloride and a surface decorated with 1% total particle weight of oxadiazon. Oxadiazon is provided to provide preemergent control or suppression of annual weeds, including goose grass, crab grass and foxtail. An 8.9 total weight percent control article is a sulfur coating on the urea.

An inventive particle is formed by coating a stainless steel pan with 500 grams of SGN 150 size 22-0-10 fertilizer core particles of the control formulation less the sulfur coating of the urea. The pan is warmed to 80 degrees C. and 25 grams of synthetic microcrystalline wax is added and brought to a melt. To the liquefied synthetic microcrystalline wax, 5 grams of polyethylene polymer is mixed and added to the fertilizer core granules with gentle agitation and a reduction of temperature which produces a complete polymer coating with a thickness of 100 microns. The coated fertilizer cores are then cooled in an airstream with gentle agitation until solidified and the temperature of the resultant coated core was less than 40° C. 6.5 grams of 10 micron average mean granule size of oxadiazon is sprinkled onto the hardened coating around the fertilizer cores. The pan is agitated for 2 minutes at 25° C. temperature to adhere a 1% by weight coating of oxadiazon to the coating.

Example 2

The control and inventive particles of the example 1 are applied to 2 foot by 3 foot plots of 419 tifway hybrid Bermuda grass growing in full sun on clay soil. The application temperatures were high temperatures averaging above 90° F. with relative humidity above 50%. Plots were replicated three times for each of the control and inventive formulation with a one foot buffer around each plot. The materials were applied at 6 lbs. of active ingredient (oxadiazon) per acre. With the materials applied, the dry foliage developed 24 hours later by irrigation watering. The results were tallied as a function of time on 0-5 scale with 0 representing no burn, 1 representing an acceptable burn, and 5 representing a severe burn. The value of a burn measured by [please insert standard]. The average of the inventive particle plots at days 5, 8, and 12 were 0.67, 0.17, and 0; whereas control plot values for the same days were 1.58, 1.25, and 1.1, respectively.

Example 3

The procedure of Example 1 is repeated. Using a 150 SGN sized particle, it also includes 10% by weight limestone. The resulting materials were applied as per example 2. In the same field trial, the comparable results obtained.

Example 4

To a 215 SGN sized 12-0-12 particle containing SGN 140 methylene urea as a nitrogen source and sulfate of potash as the potassium source, along with 10% limestone. Control and inventive particles are formed as per example 1. The resultant inventive particles at 5, 8, and 12 days after application of the field trial per example 2 had a measured burn of 1.08, 1.08, and 0.92, at 5, 8, and 12 days; whereas the control for this formulation in averaged burn values of 1.5, 1.42, and 1.25, respectively.

Example 5

The process of example 1 is repeated with the coating polymer being a 3 micron thick layer of polyurethane. Field trial results comparable to those of Example 2 are obtained.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A safened active agent coated particle comprising:
   a fertilizer core having a surface;
   a biologically active agent in a form selected from the group consisting of: powder, or granule; and
   an intermediate hydrophobic coating on the surface of said fertilizer core to which active agent is adhered.

2. The particle of claim 1, further comprising a friable layer at a position selected from the group consisting of: intermediate between said fertilizer core and said coating and above said coating.

3. The particle of claim 2, wherein said friable layer is sulfur.

4. The particle of claim 2, wherein said friable layer is rubber.

5. The particle of claim 1, wherein said coating has a thickness of 0.5 and 1000 microns.

6. The particle of claim 1, wherein said coating comprises polyurethane.

7. The particle of claim 1, wherein more than 70 weight percent of a water soluble fertilizer within said fertilizer core is retained within said core after said particle has been immersed in water for 5 minutes.

8. The particle of claim 7, wherein more than 70 weight percent of said water soluble fertilizer within said fertilizer core is retained within said core after said particle has been immersed in water for 1 minute.

9. The particle of claim 1, wherein said 70% of a water soluble fertilizer within said fertilizer core is retained within said core after said particle has been immersed in water for 0.5 seconds.

10. The particle of claim 1, further comprising a second fertilizer layer between said intermediate hydrophobic coating and said active agent granule, said second fertilizer layer being independent of water soluble nitrogen.

11. The particle of claim 1, wherein said active agent granule is at least in part embedded in said hydrophobic coating.

12. A safened active agent coated particle comprising:
   a fertilizer core containing at least 20 units of water soluble fertilizer comprising at least element selected from the group consisting of: nitrogen, phosphorous, and potassium, said fertilizer core having a surface;

an active agent granule inducing a phytotoxic chemical burn to target foliage through contact with said foliage, said granule having a size less than 10% of a diameter of said fertilizer core; and an intermediate hydrophobic coating on the surface of said fertilizer core having a thickness of between 0.5 and 1000 microns and to which said granule is adhered.

13. The granule of claim 12 further comprising a friable layer intermediate between said fertilizer granule and said coating.

14. The granule of claim 12 wherein said friable layer is sulfur.

15. The granule of claim 12 wherein said friable layer is rubber.

16. The particle of claim 12, wherein said coating comprises polyurethane.

17. The particle of claim 12, wherein more than 70 weight percent a water soluble fertilizer within said fertilizer core is retained within said core after said particle has been immersed in water for 5 minutes.

18. The particle of claim 12, further comprising a second fertilizer layer between said intermediate hydrophobic coating and said active agent granule, said second fertilizer layer being independent of water soluble nitrogen.

19. The particle of claim 12, wherein said active agent granule is at least in part embedded in said hydrophobic coating.

* * * * *